US008418535B2

(12) United States Patent
Manalis et al.

(10) Patent No.: US 8,418,535 B2
(45) Date of Patent: Apr. 16, 2013

(54) METHOD AND APPARATUS FOR INTEGRATED MEASUREMENT OF THE MASS AND SURFACE CHARGE OF DISCRETE MICROPARTICLES USING A SUSPENDED MICROCHANNEL RESONATOR

(75) Inventors: Scott Manalis, Cambridge, MA (US); Thomas Burg, Goettingen (DE); Philip Dextras, Tokyo (JP)

(73) Assignee: Massachusetts Institute of Technology, Cambridge, MA (US)

( * ) Notice: Subject to any disclaimer, the term of this patent is extended or adjusted under 35 U.S.C. 154(b) by 365 days.

(21) Appl. No.: 12/799,922

(22) Filed: May 4, 2010

(65) Prior Publication Data
US 2011/0271747 A1    Nov. 10, 2011

(51) Int. Cl.
*G01N 29/00* (2006.01)
(52) U.S. Cl.
USPC ............................... 73/64.53; 73/61.49
(58) Field of Classification Search ............... 73/61.49, 73/64.53
See application file for complete search history.

(56) References Cited

U.S. PATENT DOCUMENTS 5,417,104 A * 5/1995 Wong ................................ 73/38
7,780,842 B2 * 8/2010 Sides et al. ................. 205/790.5

* cited by examiner

*Primary Examiner* — Hezron E Williams
*Assistant Examiner* — Rodney T Frank
(74) *Attorney, Agent, or Firm* — Mark Rodgers

(57) ABSTRACT

Measurements of the mass and surface charge of microparticles are employed in the characterization of many types of colloidal dispersions. The suspended microchannel resonator (SMR) is capable of measuring individual particle masses with femtogram resolution. The high sensitivity of the SMR resonance frequency to changes in particle position in the SMR channel is employed to determine the electrophoretic mobility of discrete particles in an applied electric field. When an oscillating electric field is applied to the suspended microchannel, the transient resonance frequency shift corresponding to a particle transit can be analyzed to extract both the buoyant mass and electrophoretic mobility of each particle. These parameters, together with the mean particle density, can be used to compute the size, absolute mass, and surface charge of discrete particles.

3 Claims, 5 Drawing Sheets

METHOD AND APPARATUS FOR INTEGRATED MEASUREMENT OF THE MASS AND SURFACE CHARGE OF DISCRETE MICROPARTICLES USING A SUSPENDED MICROCHANNEL RESONATOR

FEDERALLY SPONSORED RESEARCH

Portions of the work leading to this application were funded by the NIH and the ARO

BACKGROUND OF THE INVENTION

This invention is based on a published work by the inventors: "Integrated Measurement of the Mass and Surface Charge of Discrete Microparticles Using a Suspended Microchannel Resonator;" Philip Dextras, Thomas P. Burg and Scott R. Manalis; *Anal. Chem.*, 2009, 81 (11), pp 4517-4523; Publication Date (Web): May 8, 2009 (Article); DOI: 10.1021/ac9005149. The contents of this article are incorporated in their entirety by reference. The invention relates to utilizing the high-resolution particle measurement capabilities of a Suspended Miccrochannel (SMR) resonator in combination with an applied oscillating electric field to provide an unprecedented single particle characterization capability Colloidal dispersions have a broad range of technological applications, including paints, pharmaceuticals, foods, photographic emulsions, ceramics, drilling muds, inks, and photonic crystals. Many of these applications require very precise control over colloidal stability and hence inter-particle interactions which are dependent on the physico-chemical properties of the particles themselves. Quantitative measures of particle properties such as the size, mass and surface charge are therefore often of value in designing systems and manufacturing processes for these applications. Measurements of particle size and surface charge are routinely performed using light scattering techniques such as phase analysis light scattering (PALS). This technique estimates the size and electrophoretic mobility of particles by measuring their average Brownian motion and their motion in an applied electric field respectively. While applicable to a wide variety of colloidal systems, PALS reports size and mobility values which represent averages over multiple particles. Hence accuracy in estimating the particle's charge, which is dependent on both the size and the mobility, can suffer from errors made in ensemble average measurements of these two parameters, both of which may be multi-modal for a complex population.

Various approaches for measuring size and electrical properties of single particles have been explored, such as the Coulter principle and mass spectrometry. Carbon nanotube-based Coulter counters are able to measure discrete-particle mobility and size, but compromises must be made between the signal-to-noise ratio (SNR) of the mobility measurement and that of the size measurement since they have inherently different optimum orifice lengths. Measurement of particle charge-to-mass ratio by time-of-flight mass spectrometry has been integrated with direct charge measurement using a Faraday disc, but because the sample must be dried, the measured charge may not accurately reflect that experienced in the desired dispersion medium for a given application.

Relatively recently, particle detection and measurement based on the use of SMR's has been developed, and shows promise of going beyond some of the limitations of conventional techniques. The SMR uses a fluidic microchannel embedded in a resonant structure, typically in the form of a cantilever or torsional structure. Fluids, usually containing target particles are flowed through the sensor, and the contribution of the flowed material to the total mass within the sensor causes the resonance frequency of the sensor to change in a measurable fashion. SMR's are typically microfabricated MEMS devices. The use of microfabricated resonant mass sensors to measure fluid density has been known in the literature for some time [P. Enoksson, G. Stemme, E. Stemme, "Silicon tube structures for a fluid-density sensor", Sensors and Actuators A 54 (1996) 558-562]. However, the practical use of resonant mass sensors to measure properties of individual particles and other entities suspended in fluid is relatively recent, as earlier fluid density sensors were not designed to measure individual particles at the micron and submicron scale.

In a body of work by common inventors and owned by the assignee of the current application, miniaturization and improvement of several orders of magnitude in mass resolution has been demonstrated. Development in the microfabrication recipes, the fluidics design, and measurement techniques are described in a number of co-pending patent applications and scientific publications. Of particular relevance is a publication by some of the current inventors, [T. P. Burg, M. Godin, S. M. Knudsen et al., "Weighing of biomolecules, single cells and single nanoparticles in fluid," Nature 446 (7139), 1066-1069 (2007)] By using the microfabrication techniques described in the references, SMR sensors have been fabricated with mass resolution of less than 1 femtogram ($10^{-15}$ g). This resolution is sufficient to detect and measure the mass of individual particles in the range of ~100 nanometers up to many microns in size, including mammalian cells. In addition, as the particle transits the SMR, the resonance frequency of the SMR is highly sensitive to its position along the SMR channel.

As SMR based techniques overcome some of the disadvantages of the prior art in terms of individual particle characterization, it would be desirable to utilize the measurement capabilities of an SMR to finely characterize mass and position and extend the range of particle characterization. In particular it is the object of this invention to provide an SMR based technique that also yields single micro-particle surface charge in addition to mass and density characterization.

SUMMARY OF THE INVENTION

In one embodiment, the invention is a Suspended Microchannel Resonator (SMR) system including a resonant structure with at least one fluid channel whose surfaces contacting the fluid are electrically insulating, an oscillating voltage source whose electrodes are disposed to produce an oscillating electric field in the fluid across the channel length, and an actuator for oscillating the resonant structure mechanically coupled to the structure whose drive means is electrically isolated from the oscillating electric field, the fluid channel and any part of the SMR structure.

In a particular version, the electrically insulating surfaces may be a thermal oxide passivation layer grown on the bulk resonant structure.

In another embodiment, the invention is a method for measuring surface charge of a target particle including the steps of 1. flowing the target particle in a fluid through the fluid channel of a resonating Suspended Micro Channel Resonator (SMR),
2. applying an oscillating voltage in the fluid across the length of the fluid channel,
3. determining the local oscillating E-field developed by the oscillating voltage for positions along the channel,
4. determining the zeta-potential of the fluid channel walls, 5. measuring the shift in SMR resonance and determining the local amplitude of particle oscillation due to elecrtrophoretic and electro-osmotic motion of the particle caused by the oscillating E-field from the resonant shift,
6. calculating the particle zeta-potential from the E-field, channel wall zeta-potential, and oscillation amplitude The invention may include measuring the particle mass and density by previously disclosed SMR measurements. With the above steps performed, sufficient information is available for calculating the particle surface charge.

BRIEF DESCRIPTION OF THE DRAWINGS

The invention will be better understood by referring to the following figures.

DETAILED DESCRIPTION OF THE INVENTION

The embodiments described herein are improved apparatus and methods that can be implemented using the microfabrication techniques, fluidics, and control electronics disclosed in the documents referenced and other publications available at the time the invention was made as a basis. Since those aspects of the invention common to previously disclosed work do not contribute to the novelty, they are not described in detail. The novelty of the current invention lies in the modifications and additions to the SMR, along with novel methods and those modifications are disclosed with enough detail that in conjunction with previously disclosed implementations permit practice of the invention. Also the term particle is interchangeably used in this application to mean any particulate substance, including cells. Also it is to be understood that fixed end cantilever SMR's are shown by way of example, but the techniques disclosed are not restricted to any particular SMR geometry.

Figure 1:
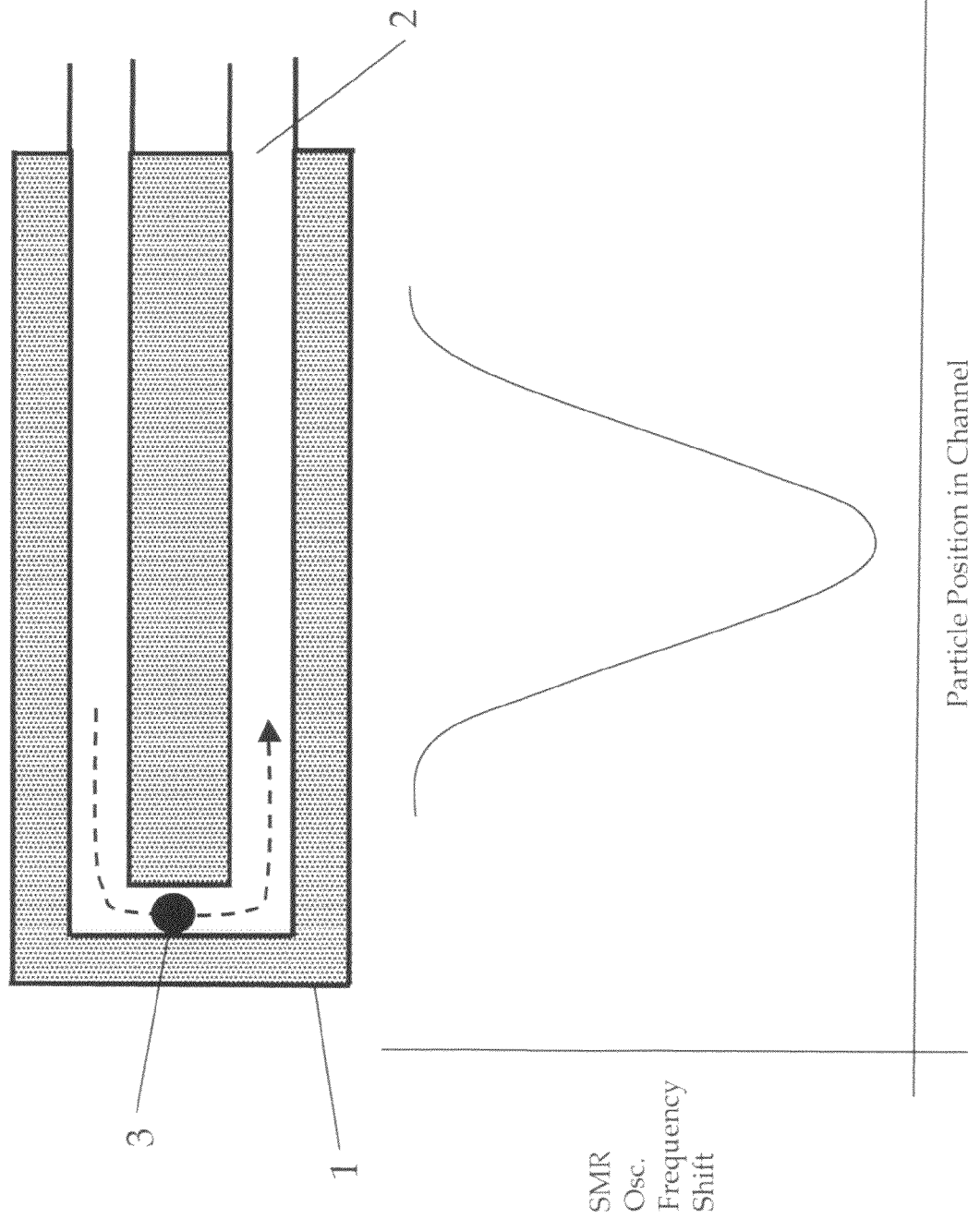
FIG. 1 is a schematic illustration of SMR resonant behavior when a particle flows through the channel.

Referring to FIG. 1 by way of review, when a particle 3 is flowed along the channel 2 of an SMR 1, an observed shift in SMR resonant frequency is dependent on the particle's position in the channel. For a cantilever type SMR, shown by way of example herein, the resonant shift is greatest when the particle is in the area nearest the end of the cantilever. Thus the resonant shift follows a curve like the idealized curve shown in the figure.

Figure 2:
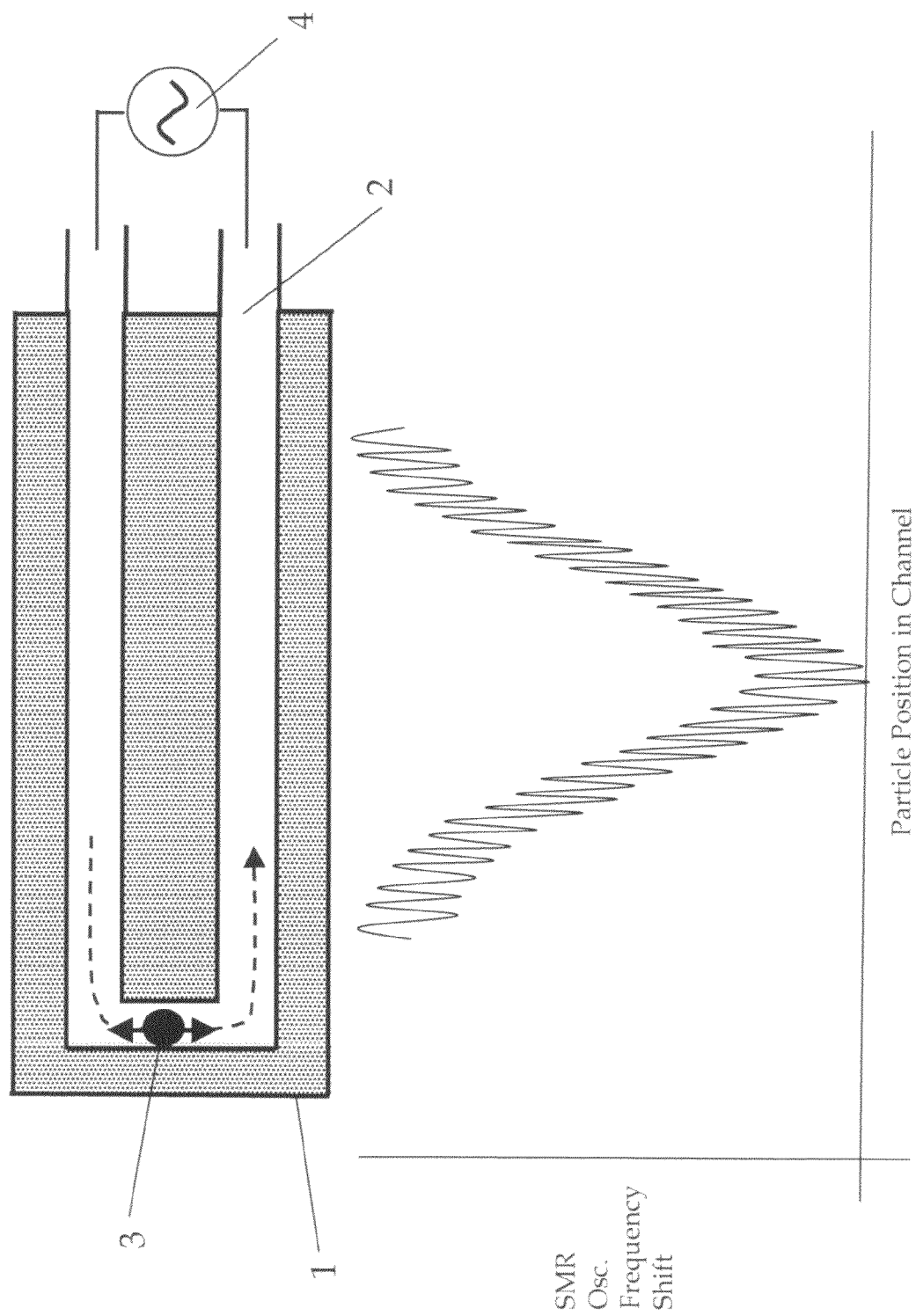
FIG. 2 depicts SMR resonant behavior when a particle flowing through it is subject to an oscillating electric field.

The inventors realized that a novel SMR set-up, including an oscillating electric field to the system, might provide the possibility for further particle characterization information. As shown in FIG. 2, if an oscillating voltage source 4 is placed in the system, such that the particle 3 experiences a suitably powerful oscillating electric field as it traverses SMR channel 2, due to electrophoretic and electro-osmotic effects, the particles course will be modulated producing an SMR frequency shift similar to the idealized curve shown in the Figure. In actual implementation the inventors indeed determined that with proper design the modulated frequency shifts could be observed with adequate signal to noise to make meaningful measurements of properties such as particle surface charge.

However improvements to the SMR set-up and measurement protocols were found important to achieving useful results.

Figure 3:
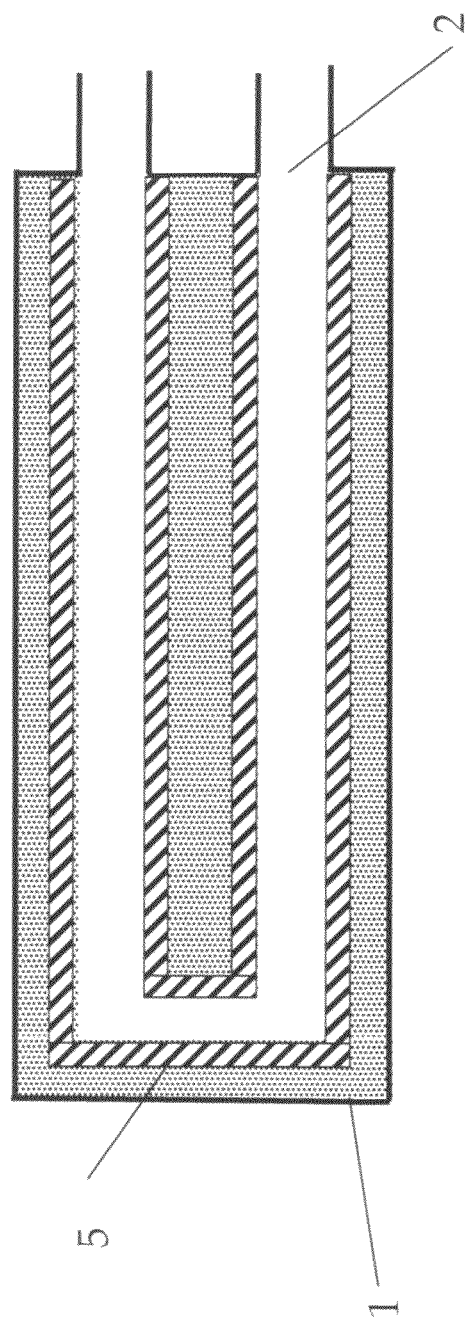
FIG. 3 depicts an SMR configured with an inner channel surface insulating layer.

SMR's of the type described herein are microfabricated MEMS devices, necessarily so to achieve the small scale and physical characteristics required for femtogram resolution. Thus necessarily the substrate materials tend to be at least partly conductive. In order to support an electric field in the fluid-filled channel, the channel needs to be electrically insulated. For a MEMS type device, a convenient way to accomplish this, as shown in FIG. 3, is to grow a passivation layer 5 on the interior walls of channel 2. In the case of a suitable SMR actually tested by the inventors, the base SMR was fabricated from silicon. In the exemplary SMR, electrical passivation of the device was accomplished by growing 800 Å of thermal oxide on all silicon surfaces contacting the fluid. Dry thermal oxide was grown at 850° C. for 15 minutes, followed by a 42 minute wet oxidation and a 30 minute dry oxidation at the same temperature. This oxide has been found to support electric fields up to 1650 V/cm in the fluid before it breaks down and shunts current through the bulk silicon.

Figure 4:
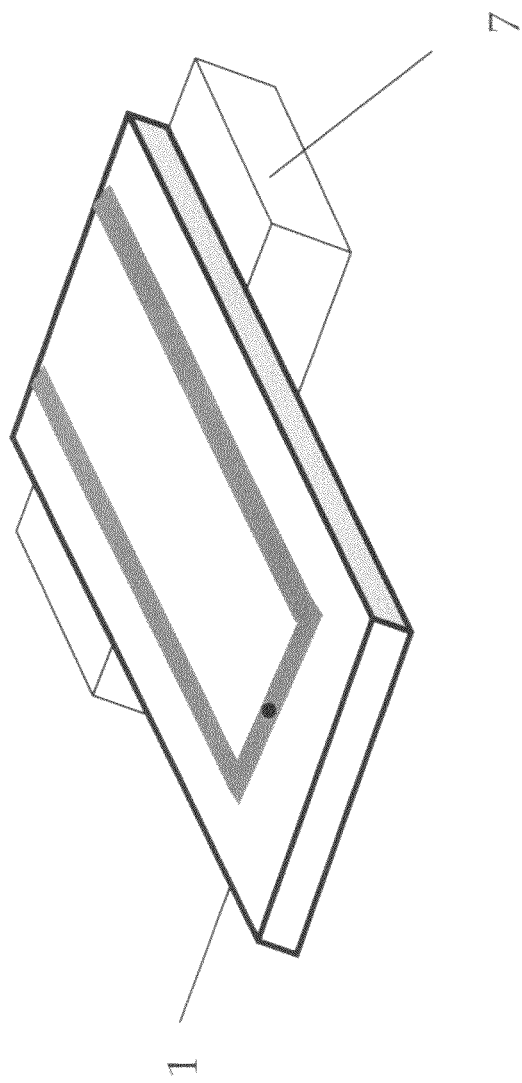
FIG. 4 depicts an SMR driven by an external actuator as opposed to the typical integrated actuators used by current devices.

In most existing SMR's including several versions disclosed by the inventors, the SMR is driven into oscillation by actuation means integrated into the SMR substrate, such as the substrate being one electrode of a piezo-resistive or electrostatic actuation scheme, as are well known in the related art of Atomic Force Microscopy (AFM) for AFM cantilever actuation. This approach is convenient because the actuation can be built into the SMR as part of the microfabrication process. But because the SMR contains a microchannel, using the SMR substrate as an electrode in the drive circuit creates a large ground plane behind the walls of this microchannel which is separated from the fluid by only the passivation oxide thickness, or some similar thin layer. The inventors observed that voltages on the order of 100 V had to be applied across the channel to achieve suitable particle movement, which translates to at least several hundreds of volts/cm across the passivation layer if the substrate is a ground plane, too close to the breakdown tolerance of a reasonable passivation layer. This situation is avoided if the bulk material (typically silicon) is allowed to float its potential to match the local fluid voltage. Therefore, as shown in FIG. 4 an external actuator 7 to drive SMR 1, whose drive means is not part of any circuit including the channel, fluid, and the substrate, is a preferable approach. In an existing implementation, actuation was performed by means of a piezoelectric crystal external to the device (PL022, Physik Instrumente GmbH & Co. KG, Karlsruhe/Palmbach, Germany). This crystal's 4 mm$^2$ footprint is small enough that it can make direct contact with the device's 145 mm$^2$ bottom surface without interfering with the optical lever beam. Contact force is adjusted by means of a set screw embedded in the manifold which seals external tubing against the device's fluid access ports on its top surface. No electrical circuit interaction exists between the piezo drive, the substrate, and the channel voltage circuit.

Figure 5:
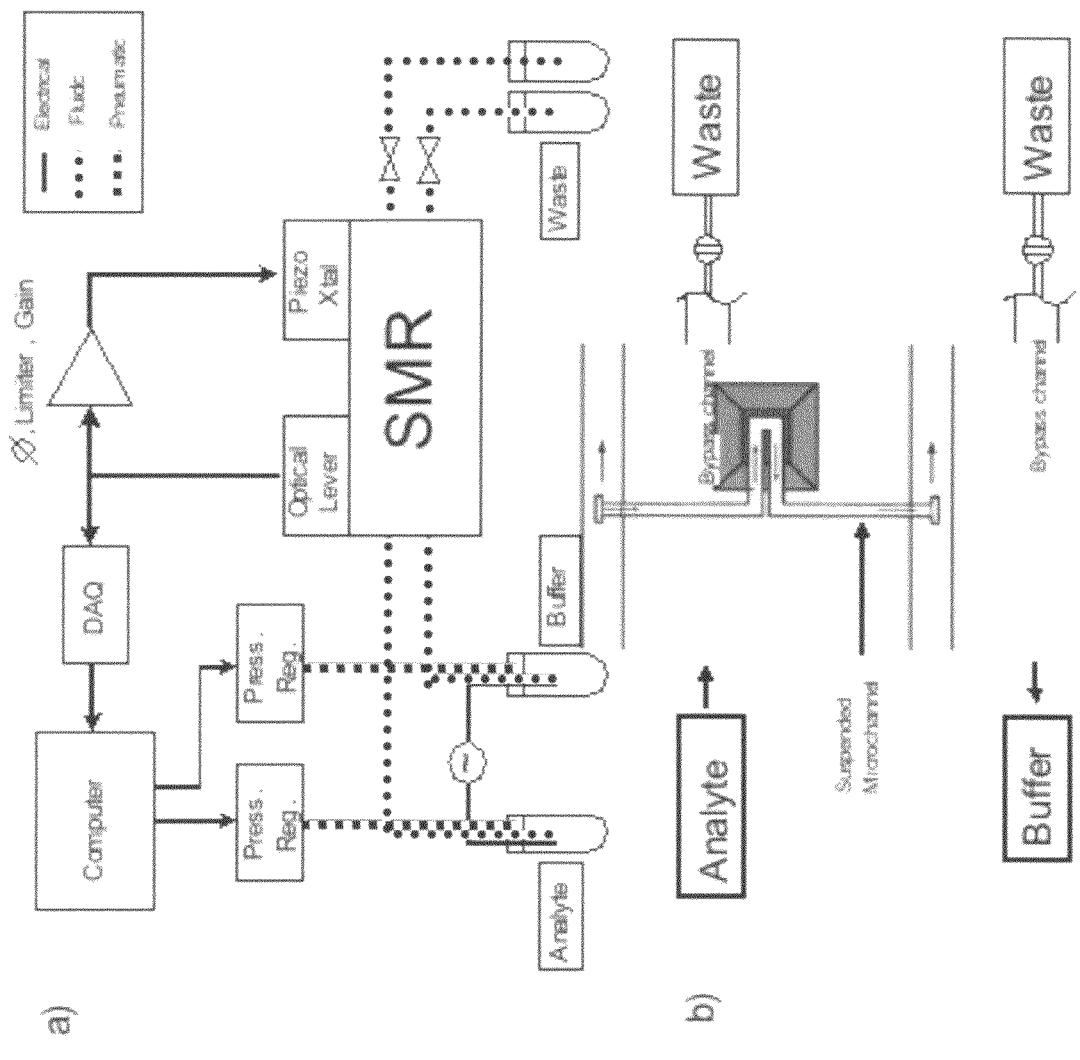
FIG. 5 is a block diagram of an implemented control system and SMR set-up

Electrodes for electrophoresis were also integrated at the system level in order to minimize complications due to electrolysis. This was accomplished using a custom manifold incorporating both platinum wire electrodes and air pressure control elements needed to achieve precise control over the particle drift velocity. A schematic of the exemplary system is shown in FIG. 5.

Given a suitable novel SMR system, behavior akin to the curve of FIG. 2 can be observed, where particle oscillations due to electrophoresis and electro-osmotic flow are measurable from the frequency shift data. This observed behavior, plus the known characterizations of the voltage source, the SMR geometry, and the ability to measure particle mass and density as previously disclosed, permit further characterization of target particles, particularly the ability to derive particle surface charge Details for the mathematical/derivations are disclosed in the referenced article, but the key steps in a novel particle characterization method are summarized herein. In particular, it is known that the surface charge of a particle may be calculated from the zeta-potential of the particle and the physical dimensions of the particle. The physical dimensions can be derived from previously disclosed techniques available from a suitable SMR, such as utilized by the present invention, improved as disclosed for the particular set-up involving an applied oscillating electric field. The zeta potential can be calculated in a system such as shown in FIG. 2 if the electric field is known, the local amplitude of oscillation due to electrophoretic and electro-osmotic flow is known, and if the channel wall zeta-potential is known. All of these parameters can be determined from knowledge of the fluid characteristics, the SMR Geometry and the applied voltage across the channel. The referenced article discloses the relationships between the various parameters, and at least one tested approach to derive the unknown parameters from known or experimentally determined information. It is to be understood that the particular protocols used for deriving the required data from known parameters described in the article are to be considered exemplary only, as one skilled in the art would conceive of other approaches to determine particular parameters.

The foregoing description of the embodiments of the present invention has shown, described and pointed out the fundamental novel features of the invention. It will be understood that various omissions, substitutions, and changes in the form of the detail of the systems and methods as illustrated as well as the uses thereof, may be made by those skilled in the art, without departing from the spirit of the invention. Consequently, the scope of the invention should not be limited to the foregoing discussions, but should be defined by appended claims.

What is claimed is:

1. A method for measuring the zeta-potential of a target particle, comprising;

flowing the target particle in a fluid through the fluid channel of a resonating Suspended Micro Channel Resonator (SMR), applying an oscillating voltage in the fluid across the length of the fluid channel, determining the oscillating E-field developed by the oscillating voltage, determining the zeta-potential of the fluid channel walls, measuring the shift in SMR resonance and determining the local amplitude of particle oscillation due to elecrtrophoretic and electro-osmotic motion of the particle caused by the oscillating E filed from the resonant shift; and, calculating the particle zeta-potential from the E-field, wall zeta-potential, and oscillation amplitude.

2. The method of claim 1 further comprising measuring at least one of the particle mass and density.

3. The method of claim 2 further comprising calculating the particle surface charge.

* * * * *